(12) United States Patent
Newell et al.

(10) Patent No.: US 8,394,377 B2
(45) Date of Patent: Mar. 12, 2013

(54) METHODS FOR TREATING CANCER USING COMBINATION THERAPY

(75) Inventors: Martha Karen Newell, Holland, TX (US); Joshua Hunter Cabrera, Colorado Springs, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 12/918,741

(22) PCT Filed: Feb. 19, 2009

(86) PCT No.: PCT/US2009/001056
§ 371 (c)(1), (2), (4) Date: Aug. 20, 2010

(87) PCT Pub. No.: WO2009/105230
PCT Pub. Date: Aug. 27, 2009

(65) Prior Publication Data
US 2010/0330087 A1   Dec. 30, 2010

Related U.S. Application Data

(60) Provisional application No. 61/066,514, filed on Feb. 21, 2008.

(51) Int. Cl.
*A61K 39/00* (2006.01)
*A61K 39/395* (2006.01)

(52) U.S. Cl. ............... 424/133.1; 424/130.1; 424/141.1; 424/143.1; 424/155.1

(58) Field of Classification Search ............ 514/23, 514/560; 424/133.1
See application file for complete search history.

(56) References Cited

U.S. PATENT DOCUMENTS

| | | |
|---|---|---|
| 4,724,213 A | 2/1988 | Epstein |
| 4,724,234 A | 2/1988 | Cone, Jr. |
| 4,935,450 A | 6/1990 | Cone, Jr. |
| 5,585,363 A | 12/1996 | Scanlon et al. |
| 5,766,571 A | 6/1998 | Ceriani et al. |
| 6,416,958 B2 | 7/2002 | Vidovic et al. |
| 6,670,330 B1 | 12/2003 | Lampidis et al. |
| 6,979,675 B2 | 12/2005 | Tidmarsh |
| 7,160,865 B2 | 1/2007 | Lampidis et al. |
| 7,390,782 B2 | 6/2008 | Newell |
| 7,445,794 B1 | 11/2008 | Newell et al. |
| 7,510,710 B2 | 3/2009 | Newell et al. |
| 7,816,319 B2 | 10/2010 | Newell |
| 8,071,645 B2 | 12/2011 | Newell et al. |
| 2002/0107234 A1 | 8/2002 | Bingham et al. |
| 2004/0116407 A1 | 6/2004 | Borisy et al. |
| 2004/0167079 A1* | 8/2004 | Tidmarsh ................... 514/23 |
| 2004/0180002 A1* | 9/2004 | Young et al. .............. 424/1.49 |
| 2005/0020682 A1* | 1/2005 | Newell et al. ............. 514/560 |
| 2005/0043250 A1 | 2/2005 | Lampidis et al. |
| 2005/0074882 A1 | 4/2005 | Newell |
| 2005/0202559 A1 | 9/2005 | Pownall |
| 2006/0019256 A1* | 1/2006 | Clarke et al. ................... 435/6 |
| 2006/0025351 A1 | 2/2006 | Lampidis et al. |
| 2006/0205757 A1 | 9/2006 | Zhang et al. |
| 2008/0181864 A1 | 7/2008 | Newell |
| 2008/0182329 A1 | 7/2008 | Newell |
| 2009/0258064 A1 | 10/2009 | Newell et al. |
| 2010/0184710 A1 | 7/2010 | Newell et al. |
| 2011/0015262 A1 | 1/2011 | Newell et al. |
| 2011/0206755 A1 | 8/2011 | Newell |
| 2011/0318335 A1 | 12/2011 | Newell et al. |
| 2012/0128724 A1 | 5/2012 | Newell |

FOREIGN PATENT DOCUMENTS

| | | |
|---|---|---|
| WO | WO 95/19765 A1 | 7/1995 |
| WO | WO 01/34145 A1 | 5/2001 |
| WO | WO 03/031643 A2 | 4/2003 |
| WO | WO 2004/043361 A2 | 5/2004 |
| WO | WO 2004/062604 A2 | 7/2004 |
| WO | WO 2004/110255 A2 | 12/2004 |
| WO | WO 2006/108276 A1 | 10/2006 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1802).*
Zips et al (In vivo, 2005, 19:1-7).*
Tai et al.(J. Controlled Release 2010 146:264-275).*
Vivi (Breast Cancer Research and Treatment 43: 15-25, 1997).*
Saydijari (Investigational New Drugs 7: 131-138, 198).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Baggetto, Deviant energetic metabolism of glycolytic cancer cells. Biochimie. Nov. 1992;74(11):959-74.
Bell et al., 2-Deoxy-D-glucose preferentially kills multidrug-resistant human KB carcinoma cell lines by apoptosis. Br J Cancer. Dec. 1998;78(11):1464-70.
Blask et al., Melatonin inhibition of cancer growth in vivo involves suppression of tumor fatty acid metabolism via melatonin receptor-mediated signal transduction events. Cancer Res. Sep. 15, 1999;59(18):4693-701.
Bui et al., Cancer's Sweet Tooth. Cancer Cell, vol. 9, Issue 6, Jun. 2006, 419-420.
Carrel et al., Recombinant interferon-gamma can induce the expression of HLA-DR and -DC on DR-negative melanoma cells and enhance the expression of HLA-ABC and tumor-associated antigens. Eur J Immunol. Feb. 1985;15(2):118-23.

(Continued)

Primary Examiner — Misook Yu
Assistant Examiner — Yan Xiao
(74) *Attorney, Agent, or Firm* — Wolf, Greenfield & Sacks, P.C.

(57) ABSTRACT

The invention relates to methods for treating a subject by manipulating HER-2 on a cell as well as related products. The methods include methods of treating cancer using fatty acid oxidation inhibitors and HER-2 binding molecules such as antibodies and fragments thereof.

13 Claims, 5 Drawing Sheets

OTHER PUBLICATIONS

Dang et al., Oncogenic alterations of metabolism. Trends Biochem Sci. Feb. 1999;24(2):68-72. Review.

Decaudin et al., Bcl-2 and Bcl-XL antagonize the mitochondrial dysfunction preceding nuclear apoptosis induced by chemotherapeutic agents. Cancer Res. Jan. 1, 1997;57(1):62-7.

Degasperi et al., Role of mitochondria in the immune response to cancer: A central role for Ca2+. J Bioenerg Biomembr. Feb. 2006;38(1):1-10. Epub Jun. 16, 2006.

Denardo et al., Effect of Lym-1 radioimmunoconjugate on refractory chronic lymphocytic leukemia. Cancer. Mar. 1, 1994;73(5):1425-32.

Derdák et al., Enhanced colon tumor induction in uncoupling protein-2 deficient mice is associated with NF-kappaB activation and oxidative stress. Carcinogenesis. May 2006;27(5):956-61. Epub Jan. 9, 2006.

Fanciulli et al., Effect of the antitumor drug Ionidamine on glucose metabolism of adriamycin-sensitive and -resistant human breast cancer cells. Oncol Res. 1996;8(3):111-20.

Fantin et al., A novel mitochondriotoxic small molecule that selectively inhibits tumor cell growth. Cancer Cell. Jul. 2002;2(1):29-42.

Fantin et al., Attenuation of LDH-A expression uncovers a link between glycolysis, mitochondrial physiology, and tumor maintenance. Cancer Cell. Jun. 2006;9(6):425-34.

Finstad et al., Effect of n-3 and n-6 fatty acids on proliferation and differentiation of promyelocytic leukemic HL-60 cells. Blood. Dec. 1, 1994;84(11):3799-809.

Halicka et al., 2-Deoxy-D-glucose enhances sensitivity of human histiocytic lymphoma U937 cells to apoptosis induced by tumor necrosis factor. Cancer Res. Jan. 15, 1995;55(2):444-9.

Harper et al., Characterization of a novel metabolic strategy used by drug-resistant tumor cells. Faseb J. Oct. 2002;16(12):1550-7.

Hayes et al., HER2 and response to paclitaxel in node-positive breast cancer. N Engl J Med. Oct 11, 2007;357(15):1496-506.

Hernlund et al., Potentiation of chemotherapeutic drugs by energy metabolism inhibitors 2-deoxyglucose and etomoxir. Int J Cancer. Jul 15, 2008;123(2):476-83.

Hu et al., A phase 1A clinical trial of LYM-1 monoclonal antibody serotherapy in patients with refractory B cell malignancies. Hematol Oncol. Mar.-Apr. 1989;7(2):155-66.

Jenski et al., Omega-3 fatty acid-containing liposomes in cancer therapy. Proc Soc Exp Biol Med. Dec. 1995;210(3):227-33.

Kaplan et al., Effects of 2-Deoxyglucose on Drug-Resistant Human Breast Cancer Cells: Toxicity and Magnetic Resonance Spectroscopy Studies of Metabolism. 1990; Cancer Res.; 50:544-551.

Kovacevic et al., "The role of glutamine oxidation and the purine nucleotide cycle for adaptation of tumour energetics to the transition from the anaerobic to the aerobic state," Biochem J. Jun. 1, 1988; 252(2): 381-386.

Kuhajda et al., Synthesis and antitumor activity of an inhibitor of fatty acid synthase. Proc Natl Acad Sci USA. Mar 28, 2000;97(7):3450-4.

Langgut, Modulation of the Proliferation and Metabolism of Tumor Cells by the Nutrition Factor, Queuine. Endocytobiosis & Cell Res. 11, 233-238 (1996).

Liu et al., Hypersensitization of tumor cells to glycolytic inhibitors. Biochemistry. May 8, 2001; 40(18): 5542-7.

Liu, Fatty acid oxidation is a dominant bioenergetic pathway in prostate cancer. Prostate Cancer Prostatic Dis. 2006;9(3):230-4. Epub May 9, 2006.

Menendez et al., Inhibition of fatty acid synthase (FAS) suppresses HER2/neu (erbB-2) oncogene overexpression in cancer cells. Proc Natl Acad Sci U S A. Jul 20, 2004;101(29):10715-20. Epub Jul. 2, 2004.

Menendez et al., The antiobesity drug Orlistat induces cytotoxic effects, suppresses Her-2/neu (erbB-2) oncogene overexpression, and synergistically interacts with trastuzumab (Herceptin) in chemoresistant ovarian cancer cells. Int J Gynecol Cancer. Jan.-Feb. 2006;16(1):219-21.

Nakamoto et al., Immune pathogenesis of hepatocellular carcinoma. J Exp Med. Jul 20, 1998;188(2):341-50.

Newell et al., Does the oxidative/glycolytic ratio determine proliferation or death in immune recognition? Ann N Y Acad Sci. 1999;887:77-82. Review.

Newell et al., Studies with glycolysis-deficient cells suggest that production of lactic acid is not the only cause of tumor acidity. 1993, Proc. Natl. Acad. Sci., vol. 90, pp. 1127-1131.

Newell et al., The effects of chemotherapeutics on cellular metabolism and cosequent immune recognition. J Immune Based Ther Vaccines. Feb. 2, 2004;2(1):3.

Nirenberg et al., Inhibition of anaerobic glycolysis in Ehrlich ascites tumor cells by 2-deoxy-D-glucose. Cancer Res. Jun. 1958;18(5):518-21.

Page et al., Principles of Chemotherapy, Cancer Management: A Multidisciplinary Approach, 7th Ed., 2003, pp. 21-37.

Papaconstantinou et al., The role of glycolysis in the growth of tumor cells. I. Effects of oxamic acid on the metabolism of Ehrlich ascites tumor cells in vitro. J Biol Chem. Feb. 1961;236:278-84.

Pelicano et al., Glycolysis inhibition for anticancer treatment. Oncogene. Aug. 7, 2006;25(34):4633-46.

Pradelli et al., Glycolysis inhibition sensitizes tumor cells to death receptors-induced apoptosis by AMP kinase activation leading to Mc1-1 block in translation. Oncogene. Mar. 18, 2010;29(11):1641-52. Epub Dec. 7, 2009.

Prentki et al., Glycerolipid metabolism and signaling in health and disease. Endocr Rev. Oct. 2008;29(6):647-76. Epub Jul. 7, 2008.

Qian et al., Mitochondrial density determines the cellular sensitivity to cisplatin-induced cell death. Am J Physiol Cell Physiol. Dec. 2005;289(6):C1466-75. Epub Aug. 17, 2005.

Rose et al., Effects of dietary omega-3 fatty acids on human breast cancer growth and metastases in nude mice. J Natl Cancer Inst. Nov. 3, 1993;85(21):1743-7.

Street et al., Interferon-gamma enhances susceptibility of cervical cancer cells to lysis by tumor-specific cytotoxic T cells. Gynecol Oncol. May 1997;65(2):265-72.

Tannock et al., Failure of 2-deoxy-D-glucose and 5-thio-D-glucose to kill hypoxic cells of two murine tumors. Cancer Res. Mar. 1983;43(3):980-3.

Thupari et al., Fatty acid synthase inhibition in human breast cancer cells leads to malonyl-CoA-induced inhibition of fatty acid oxidation and cytotoxicity. Biochem Biophys Res Commun Jul. 13, 2001;285(2):217-23.

Tolomeo et al., Drug resistance and apoptosis in cancer treatment: development of new apoptosis-inducing agents active in drug resistant malignancies. Curr Med Chem Anticancer Agents. May 2002;2(3):387-401.

Tschmelitsch et al., Enhanced antitumor activity of combination radioimmunotherapy (131I-labeled monoclonal antibody A33) with chemotherapy (fluorouracil). Cancer Res. Jun. 1, 1997;57(11):2181-6.

Tsuruo et al., Molecular targeting therapy of cancer: drug resistance, apoptosis and survival signal. Cancer Sci. Jan. 2003;94(1):15-21.

Vidović et al., Selective apoptosis of neoplastic cells by the HLA-DR-specific monoclonal antibody. Cancer Lett. Jun. 19, 1998;128(2):127-35.

Visonneau et al., Conjugated linoleic acid suppresses the growth of human breast adenocarcinoma cells in SCID mice. Anticancer Res. Mar.-Apr. 1997;17(2A):969-73.

Waki et al., Reassessment of FDG uptake in tumor cells: high FDG uptake as a reflection of oxygen-independent glycolysis dominant energy production. Nucl Med Biol. Oct. 1997;24(7):665-70.

Whelan et al., Cancer immunotherapy: an embarrassment of riches? Drug Discov Today. Mar. 15, 2003;8(6):253-8.

Wu, Control Mechanisms of Glycolysis in Ehrlich Ascites Tumor Cells. J. Biol. Chem. 1965 240: 2827-2832.

Zhelev et al., Phenothiazines suppress proliferation and induce apoptosis in cultured leukemic cells without any influence on the viability of normal lymphocytes. Phenothiazines and leukemia. Cancer Chemother Pharmacol. Mar. 2004;53(3):267-75. Epub Dec. 9, 2003.

* cited by examiner

METHODS FOR TREATING CANCER USING COMBINATION THERAPY

RELATED APPLICATIONS

This application is a national stage filing under 35 U.S.C. §371 of international application PCT/US2009/001056, filed Feb. 19, 2009, which was published under PCT Article 21(2) in English, and claims the benefit under 35 U.S.C. §119(e) of U.S. Provisional Application Ser. No. 61/066,514, entitled "METHODS FOR TREATING CANCER USING COMBINATION THERAPY" filed on Feb. 21, 2008, the disclosures of which are incorporated by reference in their entireties.

BACKGROUND OF INVENTION

Breast cancer is the most common type of cancer in women and accounts for approximately 15% of the cancer-related deaths in the U.S. HER-2, also described as c-erbB-2 or neu, is a cell surface receptor that belongs to a family of receptors that have been shown to promote cell growth, differentiation, and survival. HER-2 expression on breast cancer cells is associated with particularly aggressive breast cancer cancers and is detected in about 25 to 30% of the diagnosed breast cancer cases. HER-2 expression is associated with poor outcome, aggressive tumor behaviors, and resistance to some therapeutic agents, including the taxanes, paclitaxel and docetaxol. However, the molecule is also a target for the monoclonal antibody therapy, herceptin (also known as trustazumab). The use of herceptin, in HER-2 expressing ductal carcinoma of the breast, in combination with chemotherapy, results in an increase in disease free survival and in disease free recurrence. HER-2 degradation, resulting from its engagement with either egf or herceptin, appears to increase sensitivity to docetaxol and herceptin-induced down regulation and has been linked to improved clinical responses. Recent studies by Slamon, et al, have shown that HER-2 overexpression promotes the growth and malignancy of mammary epithelial cells, in part, by conferring resistance to the growth inhibitory effects of TGF-beta. Interestingly, however, their work also shows that HER-2 and TGF-beta signaling pathways can cooperate to promote especially aggressive disease behavior in the context of a highly invasive breast tumor model (Wilson C A et al. 2005. HER-2 overexpression differentially alters transforming growth factor-beta responses in luminal versus mesenchymal human breast cancer cells. Breast Cancer Res. 2005;7(6):R1058-79).

SUMMARY OF INVENTION

The invention is based at least in part on the discovery that fatty acid oxidation inhibitors induce HER-2 expression on cancer cells. The fatty acid oxidation inhibitor treatment causes the cells to become susceptible to further treatment with compounds that bind to HER-2. Thus, the fatty acid oxidation inhibitors may be employed as an adjunctive therapy to sensitize cancer cells to anti-HER-2 therapies, especially in those patients with HER-2 lo/negative cancers.

In some aspects the invention relates to a method of treating cancer involving the administration to a subject having cancer an effective amount of a fatty acid oxidation inhibitor and an anti-human epidermal growth factor receptor 2 (HER-2) antibody to treat the cancer.

In other aspects the invention is a method of treating cancer by administering to a subject having a HER-2 lo/negative cancer an effective amount of a fatty acid oxidation inhibitor to induce expression of HER-2 on a cancer cell and an anti-HER-2 antibody.

A method for treating cancer by identifying a subject having a HER-2 lo/negative cancer, and administering to the subject an effective amount of a fatty acid oxidation inhibitor to induce expression of HER-2 on a cancer cell is provided according to other aspects of the invention.

In another aspect the invention is a method for inducing expression of HER-2 on a cell by contacting the cell with an effective amount of a fatty acid oxidation inhibitor to induce expression of HER-2 on the cell.

In some embodiments the fatty acid oxidation inhibitor comprises at least one of etomoxir, cerulenin, 5-(tetradecyloxy)-2-furoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, or beta-hydroxy butyrate. In some embodiments the anti-HER-2 antibody is a humanized monoclonal antibody.

The cancer may be breast cancer. Additionally the cancer may be a HER-2 lo/negative cancer. The methods may involve the further step of identifying the subject as a subject that has a HER-2 lo/negative cancer.

The method may also involve administration of other agents such as a chemotherapeutic agent and/or a glycolytic inhibitor.

In yet other aspects of the invention a kit is provided. The kit includes one or more containers housing a fatty acid oxidation inhibitor and an anti-HER-2 antibody, and instructions for administering the fatty acid oxidation inhibitor and anti-HER-2 antibody to a subject having a HER-2 lo/negative cancer. In some embodiments the kit comprises two containers, one housing the fatty acid oxidation inhibitor and a second container housing the anti-HER-2 antibody. In some embodiments the fatty acid oxidation inhibitor comprises at least one of etomoxir, cerulenin, 5-(tetradecyloxy)-2-furoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, or beta-hydroxy butyrate. The anti-HER-2 antibody in some embodiments is a humanized monoclonal antibody.

In other embodiments the kit may include a third container housing an agent such as a chemotherapeutic agent or a glycolytic inhibitor.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 is a series of graphs depicting HER-2 expression in MCF7 and MCF7 ADR cells alone or treated with fatty acid oxidation inhibitors for 24 hours.

FIG. 2 is a series of graphs depicting HER-2 expression in MCF7 and MCF7 ADR cells alone or treated with fatty acid oxidation inhibitors for 48 hours.

FIG. 3 is a series of graphs depicting HER-2 expression in MCF7 ADR cells alone or treated with etomoxir for 48 hours.

DETAILED DESCRIPTION

Figure 1A:
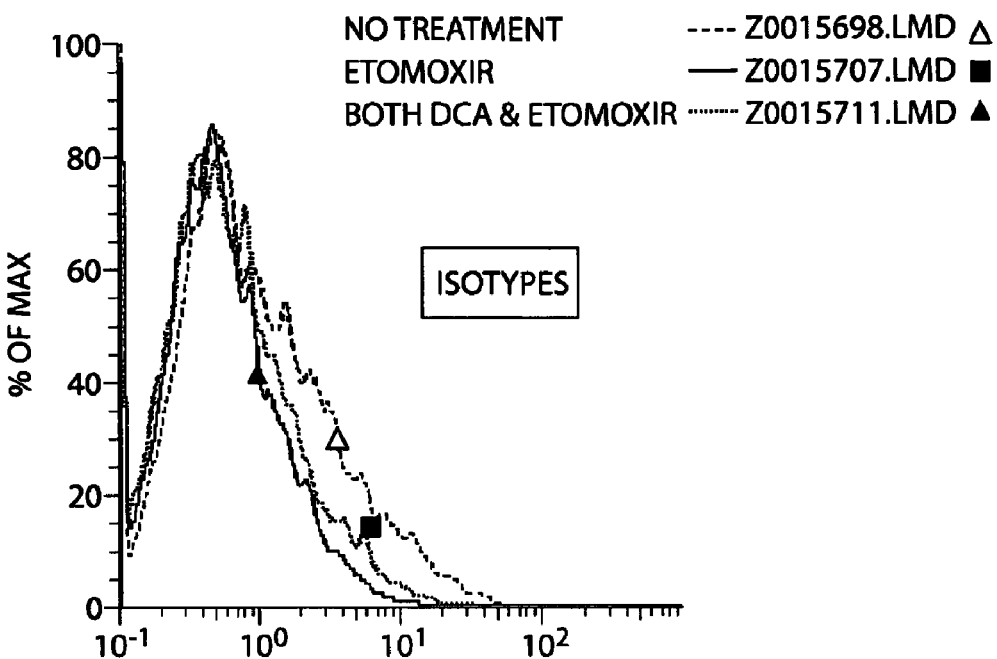
FIG. 1(A) shows a flow cytometry diagram depicting MCF7 cells that have been treated for 24 hours with etomoxir (■), DCA+etomoxir (■) or with no treatment (Δ) and stained with isotype control antibody.
Figure 1B:
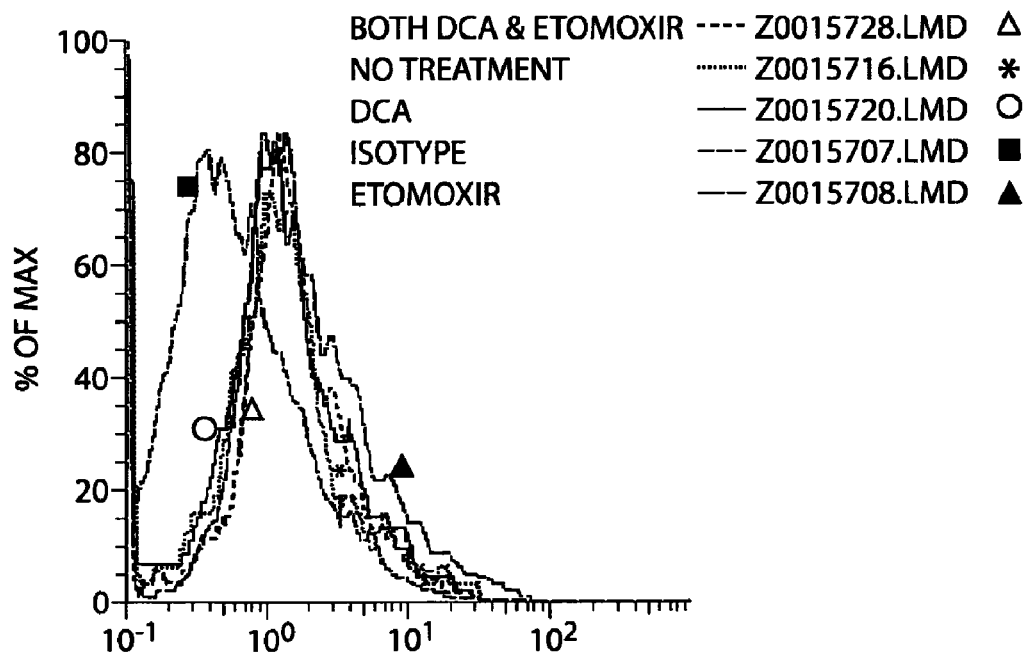
FIG. 1(B) shows a flow cytometry diagram depicting MCF7 cells that have been treated for 24 hours with etomoxir (■), DCA (○), DCA+etomoxir (Δ) or with no treatment (*) and stained with HER-2 antibody or iso type (■).
Figure 1C:
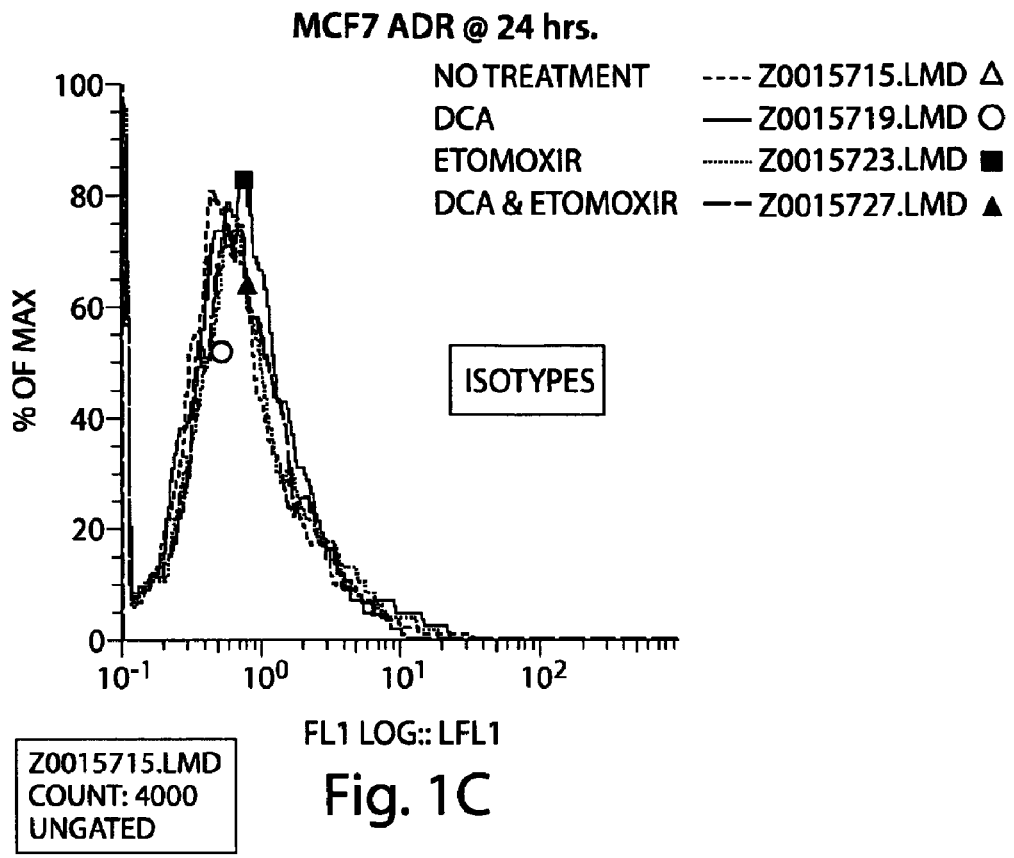
FIG. 1(C) shows a flow cytometry diagram depicting MCF7 ADR cells that have been treated for 24 hours with etomoxir (■), DCA (○), DCA+etomoxir (■) or with no treatment (Δ) and stained with isotype control antibody.
Figure 1D:
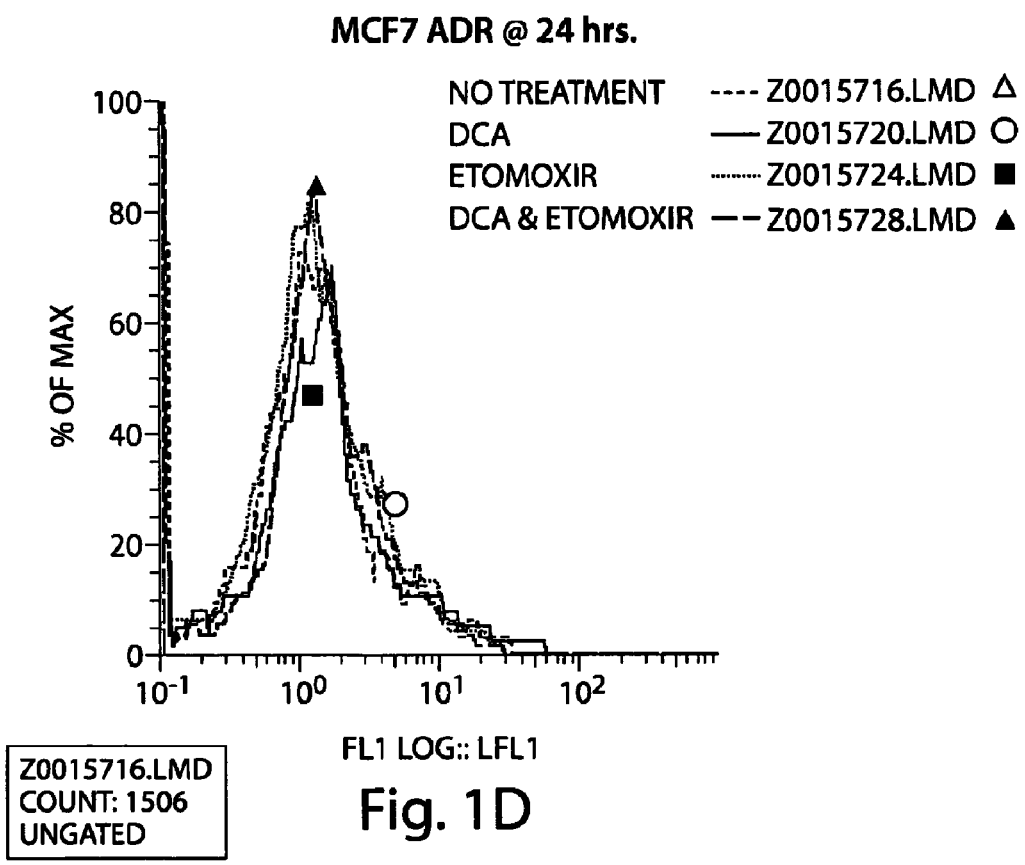
FIG. 1(D) shows a flow cytometry diagram depicting MCF7 ADR cells that have been treated for 24 hours with etomoxir (■), DCA (○) DCA+etomoxir (■) or with no treatment (Δ) and stained with HER-2 antibody.
Figure 2A:
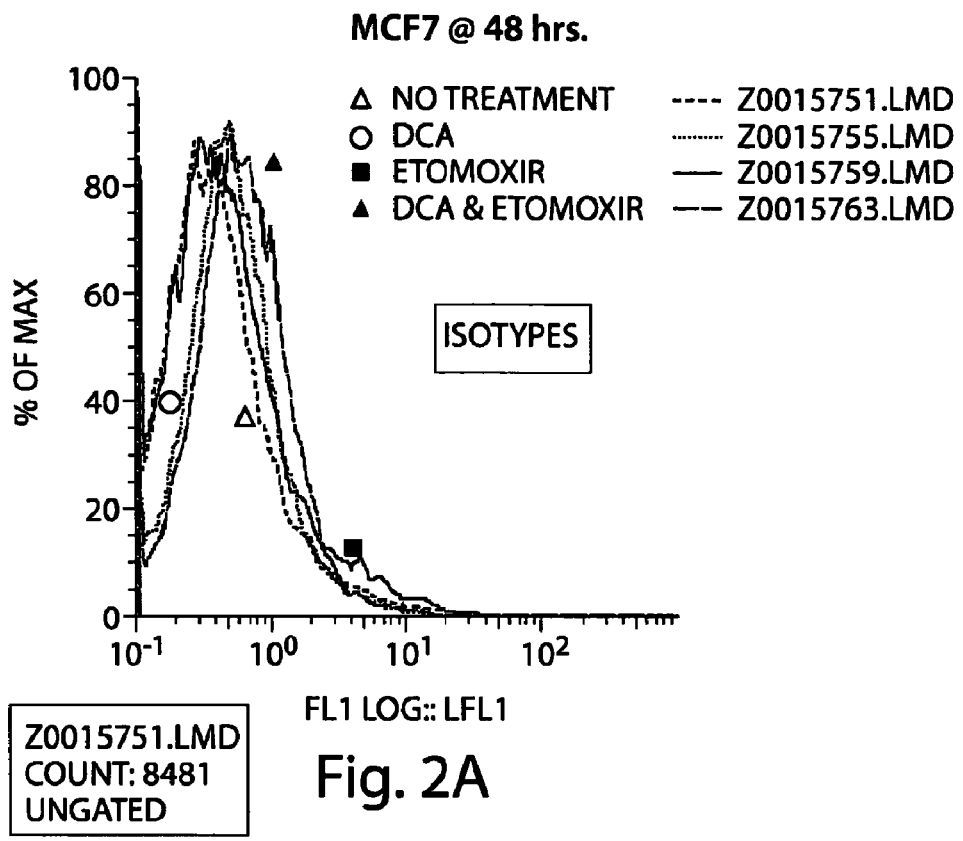
FIG. 2(A) shows a flow cytometry diagram depicting MCF7 cells that have been treated for 48 hours with DCA (○), etomoxir (■), DCA+etomoxir (■) or with no treatment (Δ) and stained with isotype control antibody.
Figure 2B:
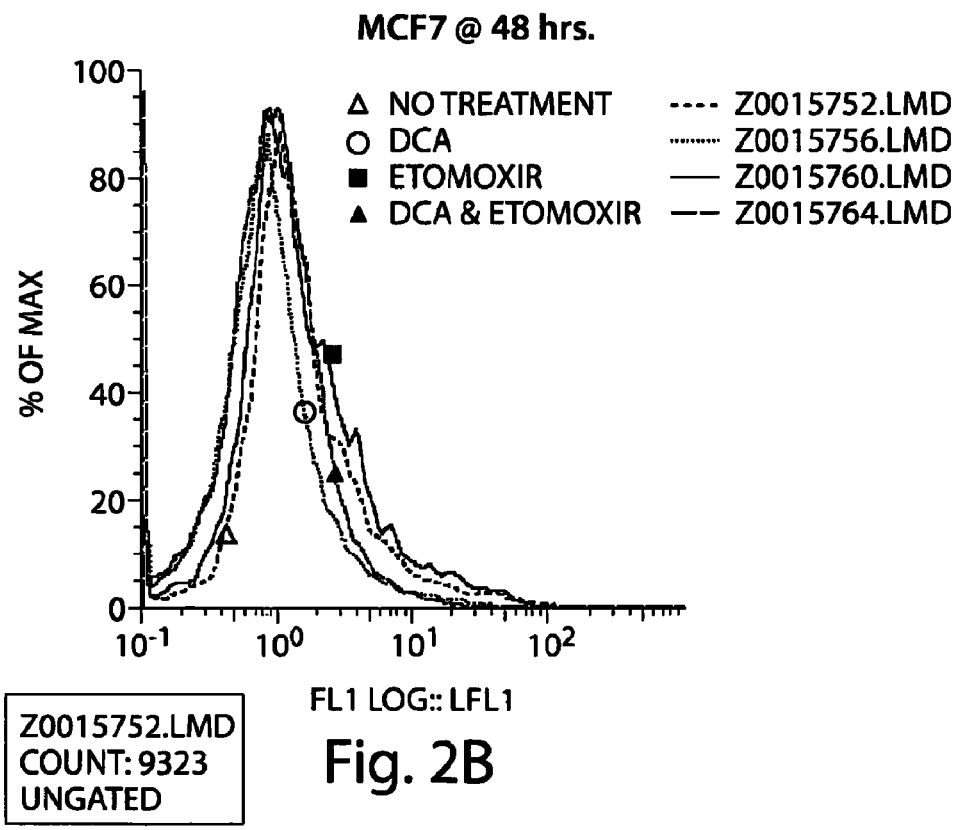
FIG. 2(B) shows a flow cytometry diagram depicting MCF7 cells that have been treated for 48 hours with etomoxir (■), DCA (○), DCA+etomoxir (■) or with no treatment (Δ) and stained with HER-2 antibody.
Figure 2C:
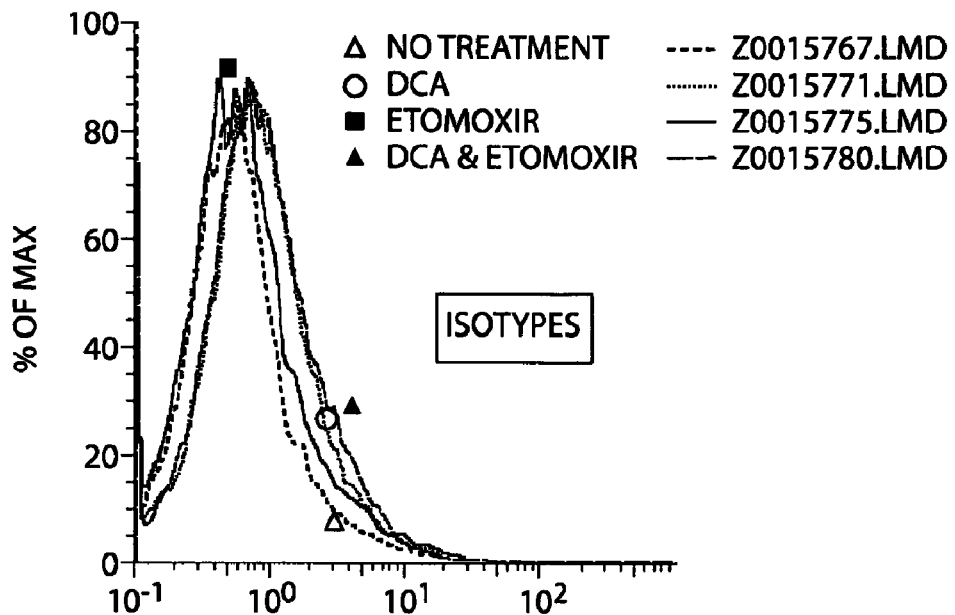
FIG. 2(C) shows a flow cytometry diagram depicting MCF7 ADR cells that have been treated for 48 hours with etomoxir (■), DCA (○), DCA+etomoxir (■) or with no treatment (Δ) and stained with isotype control antibody.
Figure 2D:
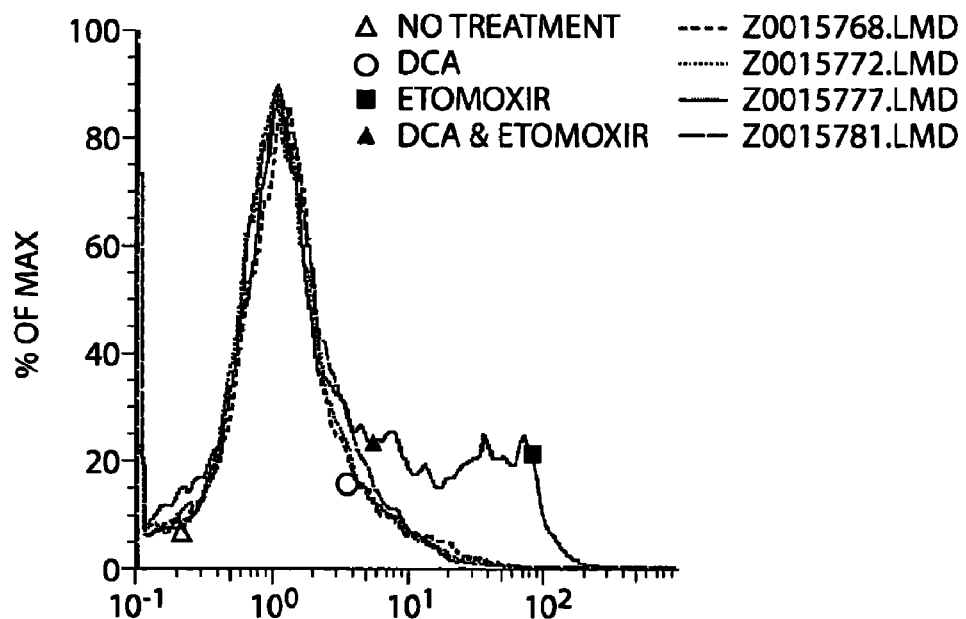
FIG. 2(D) shows a flow cytometry diagram depicting MCF7 ADR cells that have been treated for 48 hours with etomoxir (■), DCA (○), DCA+etomoxir (■) or with no treatment (Δ) and stained with HER-2 antibody.

Every cell in the body, either alone, or as a part of a tissue or organ, uses carbohydrates, protein, or fat in different proportions to insure that the cell has sufficient energy to perform its normal function. The cell's choice of fuel, i.e. the cell's metabolic strategy, will change depending on its activation or differentiation state as well as its environment. For example, a cell that is dividing has different energy demands than one that is non-dividing and, thus, must employ an alternative metabolic strategy. Another example would be the change in strategy for a cell that has been damaged by infection or stress.

The invention is focused on a mechanism of action that interferes with metabolic features of cancer, ie disruption of the strategy of these abnormally proliferating cells. We have demonstrated that cancer cells, particularly multi-drug resistant variants, selectively use a distinct mechanism to meet their energy demands. Growth factors such as epidermal growth factor can trigger many elements of signal transduction pathways that are needed for cell division. In cancer cells, these pathways are constitutively active. The result, in a bioenergetic way, is an increased rate of glycolysis in the cytosol of the cell and a predominant use of glucose oxidation in the mitochondria. In some cases, this "metabolic deviation" results in an over-expression of growth factor receptors and in other cases, the growth factor receptor as a function of the state of differentiation in which the tumor cell is locked, results in negative regulation of the growth factor receptor. In these cells, oxidative stresses, such as radiation or some chemotherapeutic agents, result in an adaptive metabolic change that appears to protect the cell from most apoptosis-inducing stimuli, including most chemotherapeutic agents and drugs. The metabolic strategy for the apoptotic resistant cells involves high rate glucose utilization (glycolysis) in the cytosol, and simultaneously the ready and preferential and selective use fatty acid oxidation as a primary source of mitochondrial fuel.

Building on our characterization of the metabolic strategies of drug sensitive and drug resistant tumor cells, we demonstrated that inhibition of fatty acid oxidation in drug resistant breast cancer cells leads to a compensatory increase in HER-2 and a consequent increase in susceptibility to chemotherapeutics and HER-2 binding molecule as adjuvant or stand alone therapy. Thus, the invention in some aspects relates to a method for inducing HER-2 expression on a cancer cell and in some cases a HER-2 lo/negative cell. HER-2 protein overexpression is observed in 25-30% of primary breast cancers. The term "HER-2" refers to human epidermal growth factor receptor 2 (also known as NGL and human c-erbB-2, or ERBB2), the human homolog of the rat proto-oncogene neu, in native-sequence or in variant form, and from any source, whether natural, synthetic, or recombinant.

Thus, the compositions of the invention may be useful in the treatment of a subject having or at risk of having cancer. A subject shall mean a human or vertebrate mammal including but not limited to a dog, cat, horse, goat and primate, e.g., monkey. Thus, the invention can also be used to treat diseases or conditions in non human subjects. For instance, cancer is one of the leading causes of death in companion animals (i.e., cats and dogs). Preferably the subject is a human.

As used herein, the term treat, treated, or treating when used with respect to a disorder such as cancer refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. A subject at risk of having cancer also includes a subject having precancerous lesions. A precancerous lesion is an area of tissue that has altered properties and carries the risk of turning into skin cancer. Precancerous lesions may be caused by, for instance, UV radiation, genetics, exposure to carcinogens such as arsenic, tar or x-ray radiation.

A subject having a cancer is a subject that has detectable cancerous cells. The cancer may be a malignant or non-malignant cancer. Cancers or tumors include but are not limited to benign and malignant tumors; leukemias and lymphoid malignancies; neuronal cancer, glial cancer, astrocytal cancer, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

In some embodiments the cancer is a HER-2 lo/negative cancer. A "HER-2 lo/negative cancer" as used herein refers to any cancer that is not HER-2 positive. A HER-2 positive cancer is one which involves overproduction of HER-2. Methods for classifying a cancer cell as a HER-2 positive or negative/lo cell are known in the art. For instance, Hayes et al, *N Engl J Med.* 2007 Oct 11;357(15):1496-506 teaches that HER2 positivity was analyzed by means of immunohistochemical analysis with the CB11 monoclonal antibody and categorized according to whether there were <50% or ≧50% positive cells.

There are many commercial antibodies available for use in research and diagnostics to detect HER2 in cancer tissues. To evaluate where a cancer cell is HER-2 positive or is a HER-2lo/negative cancer cell such antibodies can be used in known assays. For instance, the tissue can be isolated from the subject and tissue samples can be stained using the known antibodies. As a control, for instance, three different clinically validated breast carcinoma formalin fixed paraffin-embedded tissue samples representing (A) High HER2 Expression (Ductal Carcinoma in Situ), (B) Medium HER2 Expression (Infiltrating Breast Carcinoma Stage III and (C) Low HER2 Expression (Infiltrating Breast Carcinoma Stage II) could be used.

Optionally, prior to the treatment the presence of HER-2 expression on a cancer cell can be detected using the binding molecules described herein. The detection methods generally involve contacting a HER-2 binding molecule with a sample in or from a subject. Preferably, the sample is first harvested from the subject, although in vivo detection methods are also envisioned. The sample may include any body tissue or fluid that is suspected of harboring the cancer cells. For example, the cancer cells are commonly found in or around a tumor mass for solid tumors.

In some aspects, the invention provides methods and kits that include HER-2 binding molecules such as peptides, antibodies, antibody fragments and small molecules. HER-2 binding molecules bind to HER-2 on the surface of cells and enhance tumor killing. The binding molecules are referred to herein as isolated molecules that selectively bind to HER-2.

Although not intending to be bound by any particular theory, it is believed that treatment of HER-2 lo/negative tumors and cancers with HER-2 binding molecules such as antibodies may fail because the tumors are not recognized by the antibodies. The fatty acid oxidation inhibitor of the invention specifically causes induction of HER-2 expression, enabling the HER-2 binding molecule to target and destroy these cells. Thus, when these molecules are used in combination the tumor cells which were previously being missed can now be killed.

According to one set of embodiments, the cells are exposed to a fatty acid metabolism inhibitor. A "fatty acid metabolism inhibitor," as used herein, is a compound able to inhibit (e.g., prevent, or at least decrease or inhibit the activity by an order of magnitude or more) a reaction within the fatty acid metabolism pathway, such as an enzyme-catalyzed reaction within the pathway. The inhibitor may inhibit the enzyme, e.g., by binding to the enzyme or otherwise interfering with operation of the enzyme (for example, by blocking an active site or a docking site, altering the configuration of the enzyme, competing with an enzyme substrate for the active site of an enzyme, etc.), and/or by reacting with a coenzyme, cofactor, etc. necessary for the enzyme to react with a substrate. The fatty acid metabolism pathway is the pathway by which fatty acids are metabolized within a cell for energy (e.g., through the synthesis of ATP and the breakdown of fatty acids into simpler structures, such as $CO_2$, acyl groups, etc.).

The fatty acid metabolism pathway includes several enzymatic reactions, which uses various enzymes such as reductases or isomerases. Specific examples of enzymes within the fatty acid metabolism pathway include 2,4-dienoyl-CoA reductase, 2,4-dienoyl-CoA isomerase, butyryl dehydrogenase, etc, as further discussed below. In one embodiment, the fatty acid metabolism inhibitor is an inhibitor able to inhibit a beta-oxidation reaction in the fatty acid metabolism pathway. In another embodiment, the inhibitor is an inhibitor for a fatty acid transporter (e.g., a transporter that transports fatty acids into the cell, or from the cytoplasm into the mitochondria for metabolism). In yet another embodiment, the inhibitor may react or otherwise inhibit key steps within the fatty acid metabolism pathway. In still another embodiment, the inhibitor may be an inhibitor of fatty acids as a source of energy in the mitochondria. For example, the inhibitor may inhibit the breakdown of intermediates such as butyryl CoA, glutaryl CoA, or isovaleryl CoA.

2,4-dienoyl-CoA reductase is an enzyme within the fatty acid metabolism pathway that catalyzes reduction reactions involved in the metabolism of polyunsaturated fatty acids. Certain fatty acids are substrates for 2,4-dienoyl-CoA reductases located within the mitochondria. In some cases, fatty acids may be transported into the mitochondria through uncoupling proteins. The uncoupling protein may, in certain instances, increase the mitochondrial metabolism to increase the availability of fatty acids within the mitochondria and/or increase the throughput of beta-oxidation within the mitochondria.

The enzyme 2,4-dienoyl-CoA isomerase is an enzyme within the fatty acid metabolism pathway that catalyzes isomerization of certain fatty acids. One step in the metabolism of certain polyunsaturated fatty acids may be protective against reactive oxygen intermediates ("ROI"). Thus, by generating substrates and antagonists for the activity of 2,4-dienyol-CoA isomerase, the metabolic production of reactive oxygen intermediates may be enhanced and/or reduced. This, in turn, may affect certain disease states, such as cancer.

Thus, it is to be understood that, as used herein, compounds useful for inhibiting fatty acid metabolism (i.e., "fatty acid metabolism inhibitors") are also useful for altering cellular production of reactive oxygen; compounds described in reference to fatty acid metabolism inhibition should also be understood herein to be able to alter reactive oxygen production within a cell. For example, by altering the ability of a cell to metabolize a fatty acid, the ability of the cell to produce reactive oxygen may also be affected, since one pathway for a cell to produce reactive oxygen intermediates is through the metabolism of fatty acids. Alteration of the production of reactive oxygen in a cell may be associated with changes in the immune profile of cells, i.e., how immune cells respond to the cell. Thus, in some cases, the production of reactive oxygen can be affected by exposing a cell to, or removing a cell from, a fatty acid metabolism inhibitor.

In a preferred embodiment of the invention, the fatty acid inhibitor is an oxirane carboxylic acid compound. In accordance with a discovery of this invention, such compounds, exemplified by etomoxir, are able to alter cellular production of reactive oxygen. Preferred oxirane carboxylic acid compounds have the formula:

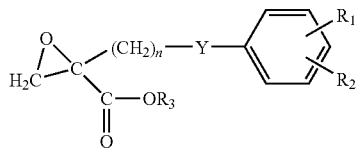

wherein: $R_1$ represents a hydrogen atom, a halogen atom, a 1-4C alkyl group, a 1-4C alkoxy group, a nitro group or a trifluoromethyl group; $R_2$ has one of the meanings of $R_1$; $R_3$ represents a hydrogen atom or a 1-4C alkyl group; Y represents the grouping —O—$(CH_2)_m$—; is 0 or a whole number from 1 to 4; and n is a whole number from 2 to 8 wherein the sum of m and n is a whole number from 2 to 8. More preferred are oxirane carboxylic acid compounds wherein $R_1$ is a halogen atom, $R_2$ is a hydrogen atom, m is 0, and n is 6, and more particularly where $R_3$ is an ethyl group.

It is most particularly preferred to use etomoxir, i.e., 2-(6-(4-chlorophenoxy)-hexyl)-oxirane-2-carboxylic acid ethyl ester. Examples of other oxirane carboxylic acid compounds useful in the invention are 2-(4-(3-chlorophenoxy)-butyl)-oxirane-2-carboxylic acid ethyl ester, 2-(4-(3-trifluoromethylphenoxy)-butyl)-oxirane-2-carboxylic acid ethyl ester, 2-(5-(4-chlorophenoxy)-pentyl)-oxirane-2-carboxylic acid ethyl ester, 2-(6-(3,4-dichlorophenoxy)-hexyl)-oxirane-2-carboxylic acid ethyl ester, 2-(6-(4-fluorophenoxy)-hexyl)-oxirane-2-carboxylic acid ethyl ester, and 2-(6-phenoxyhexyl)-oxirane-2-carboxylic acid ethyl ester, the corresponding oxirane carboxylic acids, and their pharmacologically acceptable salts.

The foregoing class of oxirane carboxylic acid compounds, including etomoxir, has been described by Horst Wolf and Klaus Eistetter in U.S. Pat. No. 4,946,866 for the prevention and treatment of illnesses associated with increased cholesterol and/or triglyceride concentration, and by Horst Wolf in U.S. Pat. No. 5,739,159 for treating heart insufficiency. The preparation of oxirane carboxylic acid compounds, and their use for blood glucose lowering effects as an antidiabetic agent, is described in Jew et al U.S. Pat. No. 6,013,666. Etomoxir has been described as an inhibitor of mitochondrial carnitine palmitoyl transferase-I by Mannaerts, G. P., L. J. Debeer, J. Thomas, and P. J. De Schepper. "Mitochondrial and peroxisomal fatty acid oxidation in liver homogenates and isolated hepatocytes from control and clofibrate-treated rats," J. Biol. Chem. 254:4585-4595, 1979. U.S. Patent Application 20030036199 by Bamdad et al, entitled: " Diagnostic tumor markers, drug screening for tumorigenesis inhibition, and compositions and methods for treatment of cancer", published Feb. 20, 2003, describes treating a subject having a cancer characterized by the aberrant expression of MUC1, comprising administering to the subject etomoxir in an amount effective to reduce tumor growth. In a preferred aspect of this embodiment, subjects for whom the methods of the invention involving treatment with etomoxir are not intended are those diagnosed with diseases which already call for treatment with etomoxir, particularly those subjects who have MUC1-dependant tumors, nor those diagnosed with diabetes, or diseases associated with increased cholesterol and/or triglyceride concentration, or chronic heart failure (e.g., failing cardiac hypertrophy associated with an inadequate sarcoplasmic reticulum function) calling for treatment with etomoxir.

The foregoing U.S. Pat. Nos. 4,946,866, 5,739,159, and 6,013,666, U.S. Patent Application 20030036199, and the foregoing publication by Mannaerts, G. P., L. J. Debeer, J. Thomas, and P. J. De Schepper, are incorporated herein by reference. In addition, U.S. patent application Ser. No. 10/272,432, filed Oct. 15, 2002, entitled "Methods for Regulating Co-Stimulatory Molecule Expression with Reactive Oxygen," by M. K. Newell, et al. is incorporated herein by reference in its entirety.

Other, non-limiting examples of fatty acid metabolism inhibitors include fatty acid transporter inhibitors, beta-oxidation process inhibitors, reductase inhibitors, and/or isomerase inhibitors within the fatty acid metabolism pathway. Specific examples of other fatty acid metabolism inhibitors include, but are not limited to, cerulenin, 5-(tetradecyloxy)-2-furoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, and beta-hydroxy butyrate. As a another example, the inhibitor may be a non-hydrolyzable analog of carnitine.

In one embodiment, the fatty acid metabolism inhibitor is a carboxylic acid. In some cases, the carboxylic acid may have the structure:

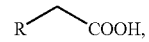

wherein R comprises an organic moiety, as further described below. In some cases, R may include at least two nitrogen atoms, or R may include an aromatic moiety (as further described below), such as a benzene ring, a furan, etc.

In another embodiment, the fatty acid metabolism inhibitor has the structure:

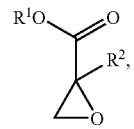

wherein each of $R_1$ and $R_2$ independently comprises organic moiety. In some instances, either or both of $R_1$ and $R_2$ may independently be an alkyl, such as a straight-chain alkyl, for instance, methyl, ethyl, propyl, etc. In certain cases, $R_2$ may have at least 5 carbon atoms, at least 10 carbon atoms, or at least 15 or more carbon atoms. For example, in one embodiment, $R_2$ may be a tetradecyl moiety. In other cases, $R_2$ may include an aromatic moiety, for example, a benzene ring. In still other cases, $R_2$ may have the structure:

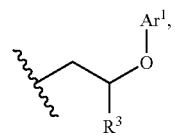

where $R_3$ comprises an organic moiety and $Ar^1$ comprises an aromatic moiety. $R_3$ may be a an alkyl, such as a straight-chain alkyl. In some instances, $Ar^1$ may be a benzene ring or a derivative thereof, i.e., having the structure: 7

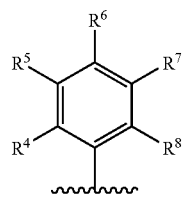

wherein each of $R_4$, $R_5$, $R_6$, $R_7$, and $R_8$ is hydrogen, a halogen, an alkyl, an alkoxy, etc.

In yet another embodiment, the fatty acid metabolism inhibitor has the structure:

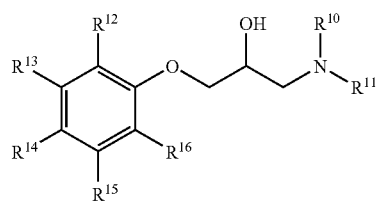

wherein each of $R_{10}$, $R_{11}$, $R_{12}$, $R_{13}$, $R_{14}$, $R_{15}$ and $R_{16}$ independently comprises hydrogen, a halogen, or an organic moiety, such as an alkyl, an alkoxy, etc. In some cases, $R_{10}$ and $R_{11}$ together may define an organic moiety, such as a cyclic group. For example, the fatty acid metabolism inhibitor may have the structure:

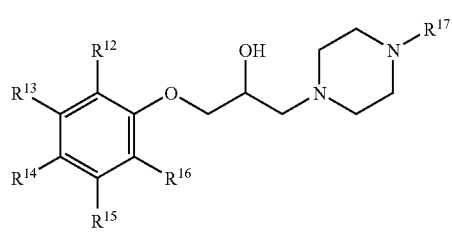

wherein $R_{17}$ comprises an organic moiety, such as an alkyl, an alkoxy, an aromatic moiety, an amide, etc. An example, of $R_{17}$ is:

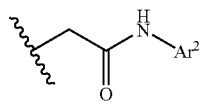

wherein $Ar^2$ comprises an aromatic moiety, such as a benzene ring or a benzene derivative, as previously described.

IN yet other embodiments the composition useful according to the invention is a bifunctional compound of a glycolytic inhibitor and a halogenated alky ester. In some embodiments the bifunctional compound has the following structure:

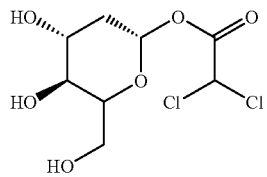

(2S,4R,5S)-4,5-dihydroxy-6-(hydroxymethyl)tetrahydro-2 H-pyran-2-yl dichloroacetate In other embodiments the bifunctional compound has the following structure:

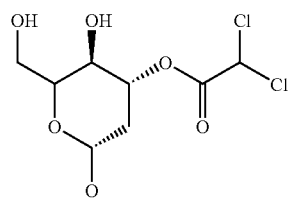

(3S,4R,6R)-3,6-dihydroxy-2-(hydroxymethyl)tetrahydro-2 H-pyran-4-yl dichloroacetate In yet other embodiments the bifunctional compound has the following structure:

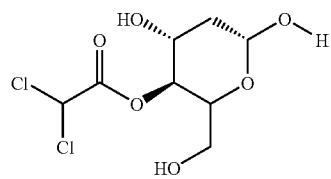

(3S,4R,6R)-4,6-dihydroxy-2-(hydroxymethyl)tetrahydro-2 H-pyran-3-yl dichloroacetate The bifunctional compound may have the following structure:

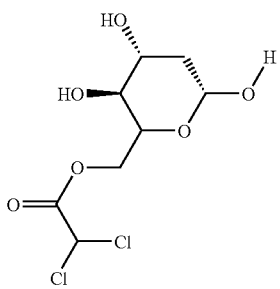

[(3S,4R,6R)-3,4,6-trihydroxytetrahydro-2 H-pyran-2-yl]methyl dichloroacetate

In still another embodiment, the fatty acid metabolism inhibitor includes a dominant negative plasma membrane polypeptide. The end result of the use (e.g., expression) of a dominant negative polypeptide in a cell may be a reduction in functional enzymes present within the fatty acid metabolism pathway. One of ordinary skill in the art can assess the potential for a dominant negative variant of a protein or enzyme, and use standard mutagenesis techniques to create one or more dominant negative variant polypeptides. For example, one of ordinary skill in the art can modify the sequence of an enzyme coding region by site-specific mutagenesis, scanning mutagenesis, partial gene deletion or truncation, and the like. See, e.g., U.S. Pat. No. 5,580,723 and Sambrook, et al., Molecular Cloning: A Laboratory Manual, Second Edition, Cold Spring Harbor Laboratory Press, 1989. One of ordinary skill in the art then can test the population of mutagenized polypeptides for diminution in a selected and/or for retention of such activity of the protein or enzyme. Other similar methods for creating and testing dominant negative variants of a protein will be apparent to one of ordinary skill in the art.

In another set of embodiments, the cells may be exposed to an agent that inhibits the synthesis or production of one or enzymes within the fatty acid metabolism pathway. Exposure of the cells to the agent thus inhibits fatty acid metabolism within the cell. For example, in one embodiment, an antisense oligonucleotide or siRNA may be used that selectively binds to regions encoding enzymes present within the fatty acid metabolism pathway, such as 2,4-dienoyl-CoA reductase or 2,4-dienoyl-CoA isomerase. Antisense oligonucleotides and siRNA are discussed in more detail below.

A molecule that selectively binds to HER-2 as used herein refers to a molecule, e.g, small molecule, peptide, antibody, fragment, that interacts with HER-2 and interferes with the HER-2 activity. In some embodiments the molecules are peptides.

The peptides minimally comprise regions that bind to HER-2. HER-2-binding regions, in some embodiments derive from the HER-2-binding regions of known or commercially available antibodies, or alternatively, they are functionally equivalent variants of such regions. The term "antibody" herein is used in the broadest sense and specifically covers intact monoclonal antibodies, polyclonal antibodies, multi-specific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Numerous HER-2 antibodies are available commercially for research purposes. For instance, Her-2 antibodies with specificity for human HER-2 are available from at least the following companies: Abcam, AbD Serotec, Abnova Corporation, ABR-Affinity BioReagents, Alpco Diagnostics, AnaSpec, ARP American Research Products, Inc., Atlas Antibodies, Beckman Coulter, Bender MedSystems, Bethyl Laboratories, BIOCARE Medical, BioGenex, BioLegend, BioVision, Calbiochem, Cell Signaling Technology, Covance Research Products, Inc, Dako, Epitomics, Inc., Exalpha Biologicals, Inc., GeneTex, GenScript Corporation, GenWay Biotech, Inc., Invitrogen, Lab Vision, Leica Microsystems Inc., Lifespan Biosciences, MBL International, Millipore Corporation, Novus Biologicals ProSci, Inc, R&D Systems, Raybiotech, Inc., Santa Cruz Biotechnology Inc., ScyTek Laboratories, Sigma-Aldrich, Signalway Antibody Co., Ltd, Spring Bioscience. Such antibodies can be used for detection or modified to enhance clinical usefulness by, for instance, any of the methods described herein.

HERCEPTIN® (Trastuzumab, Genentech Inc, South San Francisco, Calif.) is a recombinant DNA-derived humanized monoclonal antibody that selectively binds to the extracellular domain of the HER-2 proto-oncogene. An original monoclonal antibody, muMAb 4D5, was humanized by inserting the complementarity-determining regions of muMAb 4D5 into the framework of a consensus human IgG1 to produce HERCEPTIN®. HERCEPTIN® binds the extracellular domain of HER2 with three times greater affinity than the parent muMAb 4D5. It also can induce antibody-dependent cellular cytotoxicity against tumor cell lines in the presence of human peripheral-blood mononuclear cells.

In recent studies, antibodies directed against the extracellular binding domain (ECD) of HER-2 have been shown to confer inhibitory effects on tumor growth in vitro and in animal models (Hudziak, R. M., et al., Mol. Cell. Biol., 9:11-65-72, 1989; Tagliabue, E., et al., Int. J. Cancer 47:933-7, 1991; Drebin, J. A., et al., Proc. Natl. Acad. Sci. USA 83:9129-33, 1986; Drebin, J. A., et al., Oncogene, 2:273-7, 1988; Drebin, J. A., et al., Oncogene, 2:387-94, 1988; and Katsumata, M., et al., Nat. Med. 1:644-8. 1995.) In addition, Phase II and III clinical trials of a recombinant humanized anti-HER-2 monoclonal antibody, HERCEPTIN®, in patients with metastatic, HER-2-overexpressing breast cancers produced an overall response rate of 15% as a single agent. HERCEPTIN® has also been shown to improve survival when combined with cytotoxic chemotherapeutics (Baselga, J., et al., J. Clin. Oncol. 14:737-44, 1996; Pegram, M. D., et al., J. Clin. Oncol., 16:2659<-71, 1988.).

The present application describes methods for treating cancer with anti-ErbB2 antibodies, such as anti-ErbB2 antibodies that block ligand activation of an ErbB receptor. Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]).

An "intact" antibody is one which comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variant thereof. Preferably, the intact antibody has one or more effector functions.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture.

"Antibody fragments" comprise a portion of an intact antibody, preferably the antigen binding or variable region of the intact antibody. Examples of antibody fragments include Fab, Fab', F(ab')$_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999)

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa (K) and lambda (λ), based on the amino acid sequences of their constant domains.

The invention in some embodiments also involves diagnostic methods aimed at detecting, in a sample or from a subject, the presence of lo/negative HER-2 cancer cells.

The diagnostic methods may employ, for instance, diagnostic FACS analysis, Western blotting, and immunohistochemistry.

The HER-2 binding peptides useful herein are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The HER-2 binding molecules bind to HER-2, preferably in a selective manner. As used herein, the terms "selective binding" and "specific binding" are used interchangeably to refer to the ability of the peptide to bind with greater affinity to HER-2 and fragments thereof than to non-HER-2 derived compounds. That is, peptides that bind selectively to HER-2 will not bind to non-HER-2 derived compounds to the same extent and with the same affinity as they bind to HER-2 and fragments thereof, with the exception of cross reactive antigens or molecules made to be mimics of HER-2 such as peptide mimetics of carbohydrates or variable regions of anti-idiotype antibodies that bind to the HER-2-binding peptides in the same manner as HER-2. In some embodiments, the HER-2 binding molecules bind solely to HER-2 and fragments thereof As used herein, a binding peptide that binds selectively or specifically to tumor cell HER-2 may also bind HER-2 from other sources and will bind with lesser affinity (if at all) to non-HER-2 derived compounds. Lesser affinity may include at least 10% less, 20% less, 30% less, 40% less, 50% less, 60% less, 70% less, 80% less, 90% less, or 95% less.

"Isolated antibodies" as used herein refer to antibodies that are substantially physically separated from other cellular material (e.g., separated from cells which produce the antibodies) or from other material that hinders their use either in the diagnostic or therapeutic methods of the invention. Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

In one embodiment, the HER-2 peptides useful in the invention are isolated intact soluble monoclonal antibodies specific for HER-2. As used herein, the term "monoclonal antibody" refers to a homogenous population of immunoglobulins that specifically bind to an identical epitope (i.e., antigenic determinant).

In other embodiments, the peptide is an antibody fragment. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford; and Pier G B, Lyczak J B, Wetzler L M, (eds). Immunology, Infection and Immunity (2004) $1^{st}$ Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', $F(ab')_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford); and Pier G B, Lyczak J B, Wetzler L M, (eds). Immunology, Infection and Immunity (2004) $1^{st}$ Ed. American Society for Microbiology Press, Washington D.C.].

The anti-HER-2 peptides of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biot, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

As an alternative to humanization, human antibodies can be generated. A "human antibody" is one which possesses an amino acid sequence which corresponds to that of an antibody produced by a human and/or has been made using any techniques for making human antibodies. This definition of a human antibody specifically excludes a humanized antibody comprising non-human antigen-binding residues. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Human monoclonal antibodies also may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner el al., *J. Immunol.*, 147: 86-95 (1991).

The invention also encompasses the use of single chain variable region fragments (scFv). Single chain variable region fragments are made by linking light and/or heavy chain variable regions by using a short linking peptide. Any peptide having sufficient flexibility and length can be used as a linker in a scFv. Usually the linker is selected to have little to no immunogenicity. An example of a linking peptide is multiple GGGGS residues, which bridge the carboxy terminus of one variable region and the amino terminus of another variable region. Other linker sequences may also be used.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from the antibody of interest, and the light chain variable region is from another immunoglobulin.

The scFvs can be assembled in any order, for example, $V_H$-linker-$V_L$ or $V_L$-linker-$V_H$. There may be a difference in the level of expression of these two configurations in particular expression systems, in which case one of these forms may be preferred. Tandem scFvs can also be made, such as (X)-linker-(X)-linker-(X), in which X are polypeptides form the antibodies of interest, or combinations of these polypeptides with other polypeptides. In another embodiment, single chain antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L/V_H$ antigen binding site at each end. Such molecules are referred to in the art as "diabodies".

Single chain variable regions may be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*, and the expressed protein may be isolated using standard protein purification techniques.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad Sci. USA, 90: 6444-6448 (1993).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Peptides, including antibodies, can be tested for their ability to bind to HER-2 using standard binding assays known in the art. As an example of a suitable assay, HER-2 can be immobilized on a surface (such as in a well of a multi-well plate) and then contacted with a labeled peptide. The amount of peptide that binds to the HER-2 (and thus becomes itself immobilized onto the surface) may then be quantitated to determine whether a particular peptide binds to HER-2. Alternatively, the amount of peptide not bound to the surface may also be measured. In a variation of this assay, the peptide can be tested for its ability to bind directly to a HER-2-expressing cell.

The invention also encompasses small molecules that bind to HER-2 and enhance tumor killing. Such binding molecules may be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding. Phage-display peptide or antibody library is also described in Brissette R et al Curr Opin Drug Discov Devel. 2006 May;9(3): 363-9.

Alternatively, binding molecules can be identified from combinatorial libraries. Many types of combinatorial libraries have been described. For instance, U.S. Pat. Nos. 5,712, 171 (which describes methods for constructing arrays of synthetic molecular constructs by forming a plurality of molecular constructs having the scaffold backbone of the chemical molecule and modifying at least one location on the molecule in a logically-ordered array); U.S. Pat. No. 5,962, 412 (which describes methods for making polymers having specific physiochemical properties); and U.S. Pat. No. 5,962, 736 (which describes specific arrayed compounds).

Other binding molecules may be identified by those of skill in the art following the guidance described herein. Library technology can be used to identify small molecules, including small peptides, which bind to HER-2 and interrupt its function. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application W095/18972, published Jul. 13, 1995 and U.S. Pat. No. 5,712,171 granted Jan. 27, 1998 and its corresponding PCT published patent application W096/22529, which are hereby incorporated by reference.

The HER-2 binding molecules described herein can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The conjugates also include an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99}m$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The sequences responsible for the specificity of the monoclonal antibodies of the invention have been determined. Accordingly, peptides according to the invention can be prepared using recombinant DNA technology. There are entities in the United States which will perform this function commercially, such as Thomas Jefferson University and the Scripps Protein and Nucleic Acids Core Sequencing Facility (La Jolla, Calif.). For example, the variable region cDNA can be prepared by polymerase chain reaction using degenerate or non-degenerate primers (derived from the amino acid sequence). The cDNA can be subcloned to produce sufficient quantities of double stranded DNA for sequencing by conventional sequencing reactions or equipment.

The compositions and methods of the invention can be enhanced by utilization in combination with other procedures for cancer and precancerous lesions. In some instances the treatment procedure involves administration of another therapeutic agent such as an anti-cancer agent, including but not limited to chemotherapeutic agents and radiation. Chemotherapeutic agents may be selected from the group consisting of methotrexate, vincristine, adriamycin, cisplatin, taxol, paclitaxel, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, dacarbazine, LY294002, PX866, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Ince-INX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARD inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The methods of the invention may be performed with therapies for treating the cancer such as surgery and radiation. Additionally the methods of the invention may involve the administration of a glycolytic inhibitor. Preferred glycolytic inhibitors are 2-deoxyglucose compounds, defined herein as 2-deoxy-D-glucos, and homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof In general glycolytic inhibitors can have the formula:

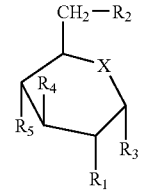

wherein: X represents an O or S atom; $R_1$ represents a hydrogen atom or a halogen atom; $R_2$ represents a hydroxyl group, a halogen atom, a thiol group, or $CO-R_6$, and $R_3$, $R_4$, and $R_5$ each represent a hydroxyl group, a halogen atom, or $CO-R_6$ wherein $R_6$ represents an alkyl group of from 1 to 20 carbon atoms, and wherein at least two of $R_3$, $R_4$, and $R_5$ are hydroxyl groups. The halogen atom is as described above with respect to the oxirane carboxylic acid compounds, and in $R_2$, $R_3$, $R_4$, and $R_5$. The halogen atom is preferably F, and $R_6$ is preferably a $C_3$-$C_{15}$ alkyl group.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

A preferred glycolytic inhibitor is 2-deoxy-D-glucose, which has the structure:

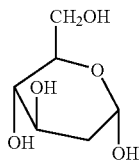

The methods of the invention may also be performed in combination with a therapeutic that is an isolated short RNA that directs the sequence-specific degradation of a specific mRNA to interfere with fatty acid metabolism through a process known as RNA interference (RNAi). The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of cancer specific mRNAs for degradation in mammalian cells useful in the therapeutic applications discussed herein.

The methods for design of the RNA's that mediate RNAi and the methods for transfection of the RNAs into cells and animals is well known in the art and the RNAi molecules are readily commercially available (Verma N. K. et al, J. Clin. Pharm. Ther., 28(5):395-404(2004), Mello C. C. et al. Nature, 431(7006)338-42 (2004), Dykxhoorn D. M. et al., Nat. Rev. Mol. Cell Biol. 4(6):457-67 (2003) Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 μmol-scale RNA synthesis provides about 1 milligram of RNA, which is sufficient for 1000 transfection experiments using a 24-well tissue culture plate format.

The cancer specific cDNA specific siRNA is designed preferably by selecting a sequence that is not within 50-100 by of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 that are hereby incorporated by reference in their entirety.

The methods described herein are used to identify or obtain RNA molecules that are useful as sequence-specific mediators of cancer specific mRNA degradation and, thus, for inhibiting proteins which contribute to the functioning of cancer cells. Expression of HER-2, for example, can be inhibited in humans in order to prevent the protein from being translated and thus preventing its function in vivo.

Any RNA can be used in the methods of the present invention, provided that it has sufficient homology to the cancer specific gene to mediate RNAi. The RNA for use in the present invention can correspond to the entire cancer specific gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 by in length. In another embodiment, the RNA is about 500 by in length.

In yet another embodiment, the RNA is about 22 by in length. In certain embodiments the preferred length of the RNA of the invention is 21 to 23 nucleotides. The Sequence of HER-2 is known, for instance, see U.S. Pat. No. 6,846,883 (which refers to HER-2 as 7p P-glycoprotein).

The HER-2 binding molecules of the invention are administered to the subject in an effective amount for treating cancer. An "effective amount for treating cancer" is an amount necessary or sufficient to realize a desired biologic effect. For example, an effective amount of a compound of the invention could be that amount necessary to c (i) kill a cancer cell; (ii) inhibit the further growth of the cancer, i.e., arresting or slowing its development; and/or (iii) sensitize a caner cell to an anti-cancer agent or therapeutic. According to some aspects of the invention, an effective amount is that amount of a compound of the invention alone or in combination with a cancer medicament, which when combined or co-administered or administered alone, results in a therapeutic response to the cancer, either in the prevention or the treatment of the cancer. The biological effect may be the amelioration and or absolute elimination of symptoms resulting from the cancer. In another embodiment, the biological effect is the complete abrogation of the cancer, as evidenced for example, by the absence of a tumor or a biopsy or blood smear which is free of cancer cells.

The effective amount of a compound of the invention in the treatment of a cancer or in the reduction of the risk of developing a cancer may vary depending upon the specific compound used, the mode of delivery of the compound, and whether it is used alone or in combination. The effective amount for any particular application can also vary depending on such factors as the cancer being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Subject doses of the compounds described herein typically range from about 0.1 μg to 10,000 mg, more typically from about 1 μg/day to 8000 mg, and most typically from about 10 μg to 100 μg. Stated in terms of subject body weight, typical dosages range from about 0.1 μg to 20 mg/kg/day, more typically from about 1 to 10 mg/kg/day, and most typically from about 1 to 5 mg/kg/day. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with a cancer medicament a sub-therapeutic dosage of either the molecules or the cancer medicament, or a sub-therapeutic dosage of both, is used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer. Therapeutic dosages of antibodies have also been described in the art.

A variety of administration routes are available. The particular mode selected will depend, of course, upon the particular anti-HER-2 antibody selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. Depending upon the type of cancer to be treated, compounds of the invention may be inhaled, ingested or administered by systemic routes. Systemic routes include oral and parenteral. Inhaled medications are preferred in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Preferred routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, e.g., the ability of the peptide to bind to HER-2.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds of the invention may be administered directly to a tissue. Preferably, the tissue is one in which the cancer is likely to arise. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations of the antibodies may be prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or nonionic surfactants such as TWEEN™, PLURONICS™ or polyethylene glycol (PEG).

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Materials and Methods

1. Cell Culture Conditions: The MCF7 and MCF7 ADR cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

2. Methods: Cells were plated into a 12 well plate with 4 mls total volume containing approximately $0.6 \times 10^6$/well for MCF7 cells and $0.8 \times 10^6$/well for MCF7 ADR cells. Treatment groups included no treatment as control; 5 mg/ml Dichloroacetate; 0.1 mg/ml Etomoxir; Both 5 mg/ml DCA and 0.1 mg/ml Etomoxir. (as shown in the table below)

The cells were incubated at 37° C. in an atmosphere containing 5% $CO_2$ and approximately 92% humidity. The cells were incubated for 24 and 48 hours. At each time point, the cells from that experimental time were harvested and stained for flow cytometric analysis of cell surface expression of HER-2/neu using anti-human HER-2 Fitc. (BD biosciences, Catalogue #340553).

Harvested cells were stained using standard fixed staining procedure that called for a 1:5 dilution of Fitc-anti-human HER-2 or isotype control. Following staining on ice for 25 minutes, cells were washed with PBS/FBS and resuspended in 100 microliters 1% paraformaldehyde and added to staining tubes containing 400 microliters of 1% paraformaldehyde. Samples were acquired and analyzed on a Coulter Excel Flow Cytometer. The staining was Direct Extracellular Staining according to the Institute of Bioenergetics protocol with the caveat that 1% paraformaldehyde is used in place of PBS/FBS for the final dilution per instruction by the manufacturer.

| Treatments for MDF7's and ADR's at 24 and 48 hrs. | |
|---|---|
| NT: | No treatments; Diluted in 1% Paraformaldehyde for flow cytometry |
| DCA | 5 mg/ml DCA; Diluted in 1% Paraformaldehyde for flow cytometry |
| Etomoxir | 0.1 mg/ml Etomoxir; Diluted in 1% Paraformaldehyde for flow cytometry |
| Both | 5 mg/ml DCA& 0.1 mg/ml Etomoxir; Diluted in 1% Paraformaldehyde for flow cytometry |
| Viability | Treatments as described; Diluted in PBS/FBS for flow to preserve viability |

Results

Figure 3A:
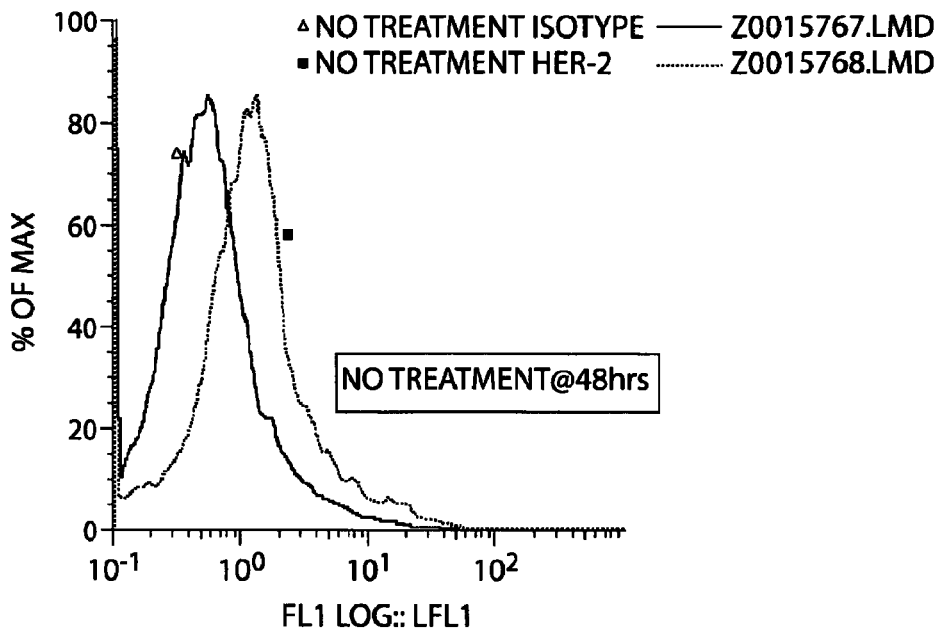
FIG. 3(A) shows a flow cytometry diagram depicting MCF7 ADR cells that have received no treatment (Δ) and stained with isotype control antibody or HER-2 antibody (■).
Figure 3B:
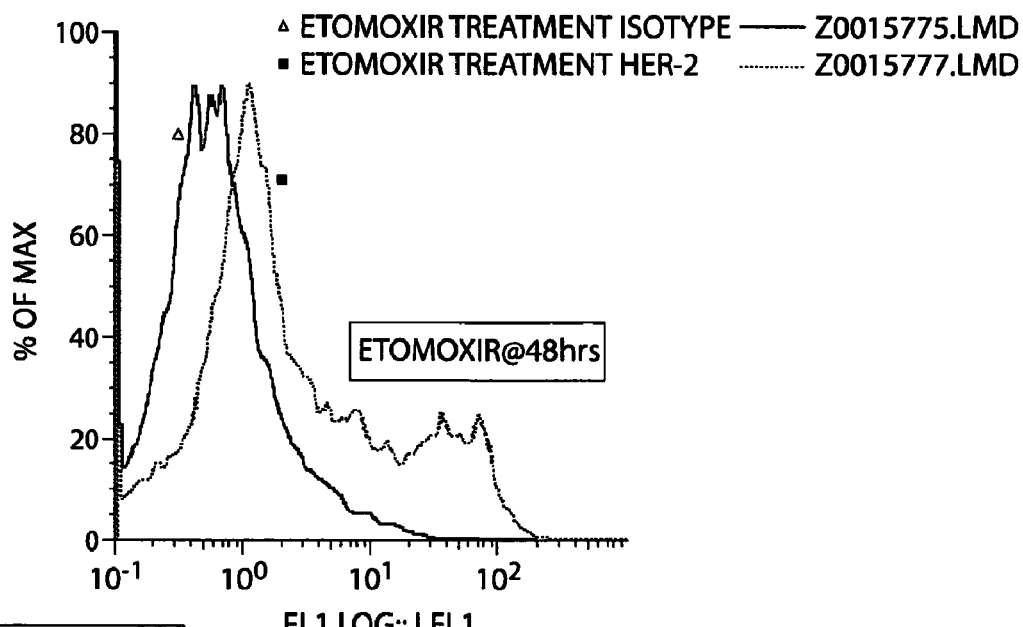
FIG. 3(B) shows a flow cytometry diagram depicting MCF7 ADR cells that have been treated for 48 hours with etomoxir and stained with isotype control antibody (Δ) or HER-2 antibody (■).

HER-2 expression on a breast cancer cell line MCF7 and a resistant subline called MCF7-Adr was examined. The results in terms of percent viability are shown in the Table below. The Expression of HER-2 in the cells at each time point is shown in FIGS. 1-3. The untreated MCF7 cells have a modest amount of cell surface HER-2; the MCF7-Adr express little to no HER-2, as seen in attached figures. The cells were treated with inhibitors of fatty acid oxidation, the compounds dichloroacetate and etomoxir. As shown in the figures etomoxir induced a major increase in HER-2 expression in the HER-2 lo/negative MCF7-Adr. At 24 hours, no effect was visible in the ADR cell lines, and the metabolic inhibitors did not cause an increase in detectable HER-2. HER-2 expression was as expected in MCF7 cell lines. At 48 hours, treatment with 0.1 mg/ml Etomoxir showed a noticeable Increase in HER-2 cell surface expression on the drug resistant MCF7 ADR cell lines.

The results in the Figures are expressed in histogram analyses. The Y axis represents cell number of the 5000 live cells versus the X axis which is a reflection of relative Fitc fluorescence. The distance between the histogram from the isotype control staining versus the histogram reflecting the specific stain is a measure of level of cell surface HER-2 on a population of live MCF7 and ADR cells as indicated.

| | Treatment | | | | | | | |
|---|---|---|---|---|---|---|---|---|
| | MCF7 NT | MCF7 DCA | MCF7 Extomoxir | MCF7 Both | MCF7 ADR NT | MCF7 ADR DCA | MCF7 ADR Etomoxir | MCF7 Both |
| % Viability | 81 | 42 | 78 | 45 | 70 | 58 | 66 | 65 |

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating breast cancer, comprising:
administering to a subject having breast cancer an effective amount of etomoxir and an anti-human epidermal growth factor receptor 2 (HER-2) antibody to treat the breast cancer, wherein the antibody is trastuzumab further comprising identifying the subject as a subject that has a HER-2 lo/ negative cancer.

2. The method of claim 1, further comprising administering a fatty acid oxidation inhibitor comprising at least one of cerulenin, 5-(tetradecyloxy)-2-firoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, or beta-hydroxy butyrate.

3. The method of claim 1, wherein the cancer is a HER-2 lo/negative cancer.

4. The method of claim 1, further comprising administering a chemotherapeutic agent to the subject.

5. The method of claim 1, further comprising administering a glycolytic inhibitor to the subject.

6. The method of claim 1, wherein the anti-HER-2 antibody is a humanized monoclonal antibody.

7. A method of treating cancer comprising:
administering to a subject having a HER-2 lo/negative cancer an effective amount of etomoxir to induce expression of HER-2 on a cancer cell and an anti-HER-2 antibody, wherein the antibody is trastuzumab and wherein the cancer is a breast cancer and wherein the cancer is resistance to chemotherapy.

8. The method of claim 7, further comprising administering a fatty acid oxidation inhibitor comprising at least one of cerulenin, 5-(tetradecyloxy)-2-furoic acid, oxfenicine, methyl palmoxirate, metoprolol, amiodarone, perhexiline, aminocarnitine, hydrazonopropionic acid, 4-bromocrotonic acid, trimetazidine, ranolazine, hypoglycin, dichloroacetate, methylene cyclopropyl acetic acid, or beta-hydroxy butyrate.

9. The method of claim 7, further comprising administering a chemotherapeutic agent to the subject.

10. The method of claim 7, further comprising administering a glycolytic inhibitor to the subject.

11. The method of claim 7, wherein the anti-HER-2 antibody is a humanized monoclonal antibody.

12. A method, comprising:
identifying a subject having a HER-2 lo/negative cancer, wherein the cancer is a breast cancer, and
administering to the subject an effective amount of etomoxir to induce expression of HER-2 on a breast cancer cell.

13. A method for inducing expression of HER-2 on a breast cancer cell, comprising contacting the breast cancer cell with an effective amount of a etomoxir to induce expression of HER-2 on the breast cancer cell.

* * * * *